US009606115B2

(12) United States Patent
Nguyen et al.

(10) Patent No.: US 9,606,115 B2
(45) Date of Patent: Mar. 28, 2017

(54) ANALYTE DETECTION METHODS AND DEVICES

(71) Applicant: NXP B.V., Eindhoven (NL)

(72) Inventors: Viet Hoang Nguyen, Leuven (BE); Filip Frederix, Heverlee (BE); Axel Nackaerts, Heverlee (BE); Youri Victorovitch Ponomarev, Leuven (BE)

(73) Assignee: NXP B.V., Eindhoven (NL)

( * ) Notice: Subject to any disclaimer, the term of this patent is extended or adjusted under 35 U.S.C. 154(b) by 13 days.

(21) Appl. No.: 14/615,714

(22) Filed: Feb. 6, 2015

(65) Prior Publication Data

US 2015/0226736 A1    Aug. 13, 2015

(30) Foreign Application Priority Data

Feb. 7, 2014 (EP) ..................... 14154371

(51) Int. Cl.
*G01N 33/543* (2006.01)
*G01N 21/84* (2006.01)
*G01N 21/59* (2006.01)
*G01N 33/558* (2006.01)

(52) U.S. Cl.
CPC ....... *G01N 33/54386* (2013.01); *G01N 21/59* (2013.01); *G01N 21/8483* (2013.01); *G01N 33/558* (2013.01)

(58) Field of Classification Search
CPC ............. G01N 33/54386; G01N 21/59; G01N 21/8483; G01N 33/558
See application file for complete search history.

(56) References Cited

U.S. PATENT DOCUMENTS

| 5,110,550 | A |   | 5/1992 | Schlipfenbacher et al. |
| 5,824,491 | A | * | 10/1998 | Priest ................ C12Q 1/28 435/14 |
| 7,738,099 | B2 |   | 6/2010 | Morrell et al. |
| 2005/0221504 | A1 |   | 10/2005 | Petruno et al. |
| 2006/0019265 | A1 |   | 1/2006 | Song et al. |
| 2007/0122914 | A1 | * | 5/2007 | Curry ............... G01N 33/54366 436/518 |
| 2008/0100464 | A1 |   | 5/2008 | Petrilla |
| 2008/0171397 | A1 |   | 7/2008 | Hardcastle et al. |
| 2008/0199971 | A1 | * | 8/2008 | Tondra .................. G01R 33/12 436/149 |

FOREIGN PATENT DOCUMENTS

| EP | 0 353 500 A2 | 2/1990 |
| WO | 2013/083686 | 6/2013 |
| WO | 2013/158505 A1 | 10/2013 |

OTHER PUBLICATIONS

Yazawa, Y., et al; "Immunoassy Device Integrating Plastic Flow-Channel Reactor and RFID Sensor Chip"; 14th Intl Conference on Miniaturized Systems for Chemistry and Life Sciences; Groningen, NL; 3 pages (Oct. 3, 2007).
Extended European Search Report for application No. 14154371.0 (Jul. 14, 2014).

* cited by examiner

*Primary Examiner* — Andrea S Grossman

(57) ABSTRACT

There is provided a lateral flow immunoassay test device. The test device comprises a test strip. The test strip comprises a test membrane having a translucent section including a control zone and a test zone. The device is adapted to house the test strip such that at least the translucent section is exposable to ambient light. The device comprises a backing structure for backing the test strip which comprises a first optical detector for detecting ambient light which has passed through the test zone, and a second optical detector for detecting ambient light which has passed through the translucent section in a further zone outside of the test and control zones. Using the detector outputs an amount of analyte in a test liquid may be calculated.

15 Claims, 4 Drawing Sheets

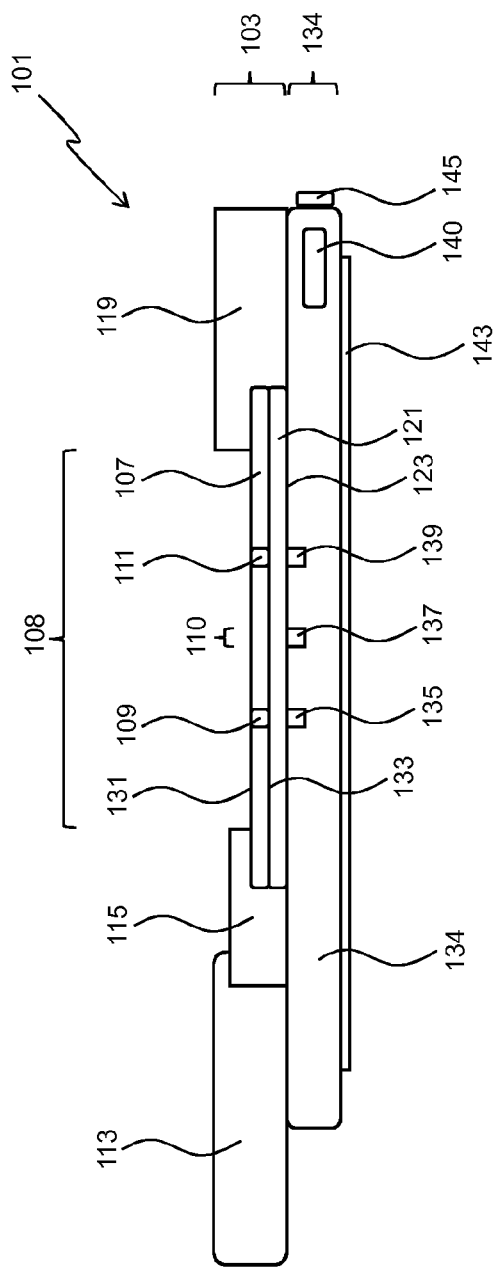
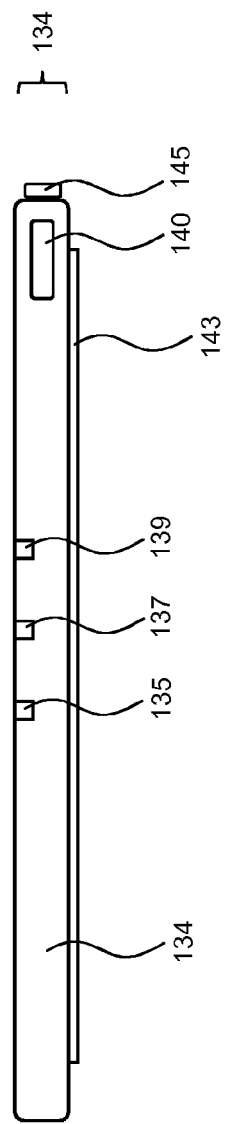

ANALYTE DETECTION METHODS AND DEVICES

CROSS-REFERENCE TO RELATED APPLICATIONS

This application claims the priority under 35 U.S.C. §119 of European patent application no. 14154371.0, filed on 7 Feb. 2014 the contents of which are incorporated by reference herein.

The present specification relates to a lateral flow immunoassay test device for detecting an analyte of interest in a test liquid.

The present specification also relates to a method of operating a lateral flow immunoassay test device to detect an analyte of interest in a test liquid.

The present specification also relates to a method of processing detector outputs, a computer program product for implementing the method and a computing device including the computer program product.

The present specification yet further relates to an assay kit comprising the test device and the computer program product and/or the computing device.

Lateral Flow Immunoassay Tests (LFTs) are very popular diagnostic tools used for quick determination of whether a target analyte is present in a sample liquid. A conventional lateral flow test apparatus comprises an elongate membrane along which a sample analyte flows. The sample analyte may or may not contain a particular analyte at a concentration level of interest. Typically, at a specific test zone, the membrane is impregnated with molecules which are chosen because they interact either with the analyte of interest, or with a labelled (marker) reagent molecule which may be conjugated with the analyte. Examples of labelled marker reagents include gold nanoparticles which are typically red and polystyrene spheres which are typically blue. The impregnated molecules are typically bioreceptors. The presence of the analyte of interest in the sample results in accumulation of a labelled reagent at the test zone. Provided the labelled reagent is optically active, once a sufficiently high concentration of labelled reagent has accumulated at the test zone, this may be observed by the user of the test apparatus. The test zone is typically defined as a test line which extends across the membrane, but does not extend significantly along it, so may have dimensions of: the width of the membrane (across the membrane) ~0.5-1.5 mm and typically 1 mm (along the membrane).

In order to avoid false-negative results (or in some instances, such as competitive assays, false positive results), lateral flow tests generally include a control zone at which labelled (marker) reagent molecules may also accumulate. The presence of a visual change at the control zone provides confirmation of adequate flow along the lateral flow test apparatus.

LFTs are used over a wide range of fields from environmental applications to consumer diagnostics. A well-known example of a LFT is a pregnancy test stick.

LFTs can provide the following principal advantages: established mature technology; reasonable sensitivity; small sample volume; relatively ease of manufacture and, therefore, volume scaling; relatively low cost.

In order to reduce the inherent subjectivity of a visual inspection by the user, it has been proposed to replace the visual inspection by an integrated optical system. The most popular LFT reader technologies are based on optical detection of light reflected from the test and control zones of the LFT membrane and an LCD panel for displaying the test result.

Yazawa et al. note that an optical-detection system has yet to be applied to conventional lateral flow immunoassays owing to the difficulty in designing a low-cost, sensitive, and compact optical-detection mechanism. Yazawa et al. suggest an alternative to the widely used conventional porous membrane as they report that porous membranes have insufficient reproducibility for quantitative measurement. Yazawa et al. propose an integrated immunoassay device (IID) consisting of two components, a reaction chamber (i.e. a flow-channel reactor) and a sensor chip for chemiluminescence detection. (Y. Yazawa et al., Immunoassay device integrating plastic flow-channel reactor and RFID sensor chip, $14^{th}$ International Conference on Miniaturized Systems for Chemistry and Life Sciences, 3-7 Oct. 2010, Groningen, The Netherlands). US 2006/0019265 proposes a luminescence detection system for use with a chromatographic-based assay device. Whilst the system of US'265 is claimed to reduce reliance on expensive optical components, such as monochromators or narrow emission bandwidth optical filters, an excitation source is required. Such excitation sources are usually relatively expensive.

It is therefore a challenge to provide cost-effective LFT arrangements.

The present specification inter alia seeks to provide a cost-effective lateral flow immunoassay test device for detecting an analyte of interest in a test liquid.

The present specification also seeks to provide a method of operating the lateral flow immunoassay test device.

The present specification also seeks to provide a method of processing detector outputs, a computer program product for implementing the method and a computing device including the computer program product.

The present specification also seeks to provide an assay kit comprising the test device and the computer program product and/or the computing device.

According to an aspect, there is provided a lateral flow immunoassay test device for a lateral flow immunoassay test strip comprising a test membrane having a translucent section including a control zone and a test zone;

the device being adapted to house the test strip such that at least the translucent section is exposable to ambient light and comprising:

a backing structure for backing the test strip comprising:

a first optical detector for detecting ambient light which has passed through the test zone, and a second optical detector for detecting ambient light which has passed through the translucent section in a further zone outside of the test and control zones;

and wherein the device is adapted to house the test strip such that the first optical detector is aligned with the test zone and the second optical detector is aligned with the further zone.

As labelled reagents are accumulated at the test zone of the membrane, the amount of ambient light to pass through the test zone will be reduced. By comparing the output of the first optical detector and the output of the second optical detector, the absorbance due to the accumulation of the labelled reagents can be determined. In turn, this means that an amount of labelled reagent accumulated at the test zone can be determined. Further, this means that ambient light is sufficient to determine an amount of reagent accumulated at the test zone, as comparison of the first and second detector outputs can enable accurate determination of an amount of labelled reagent present in the test zone. In turn, this can enable determination of an amount of analyte present in the sample.

As the membrane of the test is filled with test liquid, the translucency of the membrane may change, e.g. it may become more translucent. This can be detected by a sudden change in the amount of ambient light passing through the test membrane. By knowing the distance between the test zone where the first detector is and the further zone where the second detector is, the flow rate of test liquid can be calculated.

This flow rate information together with the amount of analyte (discussed above) may permit quantification of the test result, e.g. as a concentration of an analyte of interest in a sample.

The development of signal over time also carries information about the kinetics of the reaction. In some circumstances this information can also be used for diagnostic purposes.

Further, this device can enable multiplexing for the detection of multiple analytes in one test. For example, there may be two or more test zones, e.g. the presence of a first analyte in the sample may lead to the accumulation of a first labelled reagent in a first test zone and the presence of a second analyte in the sample may lead to the accumulation of a second labelled reagent in a second test zone. The absorbance in both test zones may be detected using two detectors, one for each test zone, and the second detector discussed above. As a further example, if the presence of a first analyte R leads to red absorbance from a first labelled reagent in the test zone and a second analyte B leads to blue absorbance a second labelled reagent in the test zone. Then, by detecting the ambient light which has passed through the test zone and observing whether red or blue light is present relative to the ambient light which has passed through the further zone, it is possible to determine whether one or both of the analytes R and B are present in the test sample and, further in combination with for instance flow rate information, to obtain a quantitative result.

Thus a lateral test apparatus according to embodiments may be able to test for more than one type of test molecule. This is particularly useful in situations in which it is desired to screen for a plurality of different test molecules, or where no one single test molecule provides a strong indicator of, for instance, a specific medical condition, but the presence of each of several types of molecules, when considered in combination, provides a stronger indication. In conventional lateral flow test apparatus a plurality of apparatuses, or a more complex testing configuration would be required, for instance requiring complex optical routing or multiple optoelectronic components. In embodiments, by replicating only a few features—such as only a further test zone, a pair of detectors, the lateral flow test can become a multiplexed test or multiplexed assay, with limited additional complexity or cost.

The backing structure may further comprise a third optical detector for detecting ambient light which has passed through the control zone. The device is also adapted to house the test strip such that the third optical detector is aligned with the control zone.

As labelled reagents are accumulated at the control zone of the membrane, the amount of ambient light to pass through the control zone will be reduced. As described above, by comparing the output from the third detector with that of the second detector, the amount of labelled reagent accumulated at the control zone can be determined. In turn, this can indicate whether the test has completed successfully.

The test device may further comprise a housing including a window for allowing the ambient light to enter the housing and pass through the translucent section.

This provides a housing to protect the test strip and/or backing structure of the test device. The window may be a transparent substrate, e.g. plastic or glass, or it may be an opening in the housing.

The test device may further comprise the test strip.

The test strip may comprise a transparent membrane backing foil. This can enable easier handling of the membrane during manufacture.

The external surface of the transparent membrane backing foil may have a matt texture.

This can maximize light diffusion when the membrane is dry and/or maximize the difference between dry and wet in terms of transparency to ambient light.

At least one of the first, second and/or third optical detectors may be integrated into the membrane backing structure, such that the detector is in close proximity with the test strip surface. Selection of the correct spacing between the detector and the test strip surface requires careful consideration, in particular, it is necessary to avoid fouling of the sensor (which can occur if the sensor is too close to the test strip), however, light pollution for undesired zones may be more likely leak into the detector if it is too far away from the strip. For example, when the test strip is housed in the test device the detector may be less than 5 mm, 3 mm, 2.5 mm, 2 mm, 1.5 mm, 1 mm, 1.0 mm, 0.75 mm, 0.50 mm, or 0.25 mm away from the test strip.

This is a simple construction which does not require a complex optical path. Further, the transition moment from dry to wet of the membrane may be reliably detected. Because the detector is close to the test strip there can be less light pollution which would otherwise adversely affect the optical detectors and therefore the test result. In other words, only ambient light which has passed through the correct zone may reach the relevant detector such that the effects of light pollution may be mitigated.

The backing structure may comprise a first sensor comprising a first array of detectors, wherein the first optical detector is one of the detectors of the first array.

This means that it is not necessary for the test zone to be in exact registration with a particular detector. Rather, the test zone may be in registration with a detector of the array. This is relevant as it can be difficult to place a test zone at a particular, pre-defined, location of a test membrane. Therefore, use of such a sensor allows greater tolerance in the placement of the test zone.

The detectors of the array may be individually readable, such that the outputs may be individually processable.

The backing structure may comprise a second sensor comprising a second array of detectors, wherein the second optical detector is one of the detectors of the second array.

As above, this can provide greater tolerance in the positioning of the various zones on the test membrane.

The detectors of the second array may be individually readable, such that the outputs may be individually processable.

If the third detector is present, the backing structure may comprise a third sensor comprising a third array of detectors, wherein the third optical detector is one of the detectors of the third array.

As above, this can provide greater tolerance in the positioning of the control zone on the test membrane.

The detectors of the third array may be individually readable, such that the outputs may be individually processable.

As used herein, an optical sensor can be understood as an array of detectors, commonly called pixels. In particular, the above first, second and/or third sensors may be part of one sensor or detector array—in other words, one (relatively large) pixelated sensor may provide the first, second and/or third sensors and hence the first, second and/or third arrays and therefore the first, second and/or third detectors. The detectors (or pixels) may be individually readable, such that the outputs may be individually processable.

The test device may further comprise a processor adapted to receive outputs from the optical detectors.

The processor may be on the same substrate as the detectors; may be in close proximity to the detectors; or may be packaged in the same package as the detectors.

The processor may be on the same substrate as the sensors, in close proximity to the sensors or packaged in the same package as the sensors.

The processor may be adapted to process said outputs.

This can enable calculation of the test result on the device itself.

The test device may further comprise an antenna for wirelessly transmitting the (processed) outputs, wherein the processor is adapted to supply the antenna with said (processed) outputs.

The test device may further comprise a port for transmitting the (processed) outputs by wire. The processor may be adapted to supply the port with said (processed) outputs.

The antenna or port can transfer the raw data or processed data by wire or wirelessly to a display/data processing host, where the test results can be displayed, archived and/or forwarded to relevant people/professionals.

According to a second aspect, there is provided a method of operating a lateral flow immunoassay test device, comprising:

providing a test device according to the first aspect housing a test strip;

applying a test liquid to the test strip;

illuminating the translucent section with ambient light;

detecting ambient light which has passed through the test zone with the first optical detector;

detecting ambient light which has passed through the translucent section in the further zone with the second optical detector; and transmitting outputs of the detectors to a processor.

This can provide advantages similar to those provided by the first aspect. Specifically, by comparing the outputs of the first and second optical detectors, the amount of labelled reagent accumulated at the test zone can be deduced.

Also as the membrane of the test is filled with test liquid, the translucency of the membrane may change, e.g. it may become more translucent. This can be detected by a sudden change in the amount of ambient light passing through the test membrane. By knowing the distance between the test zone where the first detector is and the further zone where the second detector is, the flow rate of the test liquid can be calculated. This information together with the amount of labelled reagent accumulated at the test zone can allow quantification of the test result, e.g. as a concentration of an analyte of interest in a sample.

The backing structure may further comprise a third optical detector for detecting ambient light which has passed through the control zone, and the method may further comprise detecting ambient light which has passed through the control zone with the third optical detector.

As labelled reagents are accumulated at the control zone of the membrane, the amount of ambient light to pass through the control zone will be reduced. As described above, by comparing the output from the third detector with that of the second detector, the amount of labelled reagent at the control zone can be determined. In turn, this can indicate whether the test has completed successfully.

The detecting of ambient light which has passed through the test zone, the further zone and/or, if detected, the control zone may comprise detecting ambient light over a period of time and transmitting the time-dependent outputs to the processor.

As detailed herein, determining timing of the (relative) changes detected by the first, second and/or third detectors may be advantageous, accordingly, the method may comprise measuring the time-dependant difference between the first, second and/or third detector outputs. Further, the device may be adapted to record, monitor and/or transmit the time-dependant outputs. Therefore, in the context of the present specification, detecting light includes the detection of a light intensity distribution over space, time and wavelength.

The test device may comprise the processor and the method may further comprise processing the outputs of the detectors on the processor to determine an amount of analyte in the test liquid.

This can enable calculation of the test result on the device itself.

The outputs of the detectors may be transmitted by wire or wirelessly to the processor.

This can enable transfer of the (processed) outputs wired or wirelessly to a display/data processing host, where the test results can be displayed, archived and/or forwarded to relevant people/professionals.

According to another aspect, there is provided a method of determining an amount of analyte in a sample, the method comprising:

receiving detector outputs transmitted by a method according to the second aspect provided above;

and processing the outputs on a processor to determine an amount of analyte in the test liquid.

The outputs may be received by wire or wirelessly.

According to another aspect, there is provided a computer program product comprising computer-readable storage means comprising computer program code for, when executed on one or more processors of a computing device, implementing the method of determining an amount of analyte in a sample provided above.

According to another aspect, there is provided a computing device including at least one processor and the computer program product provided above wherein at least one processor is adapted to execute the code of said product.

The computing device could receive the raw data or processed data by wire or wirelessly and act as a display/data processing host, where the test results can be displayed, archived and/or forwarded to relevant people/professionals. For example, the second device could encrypt and broadcast the test results to targeted receivers.

Optionally the computing device is a mobile phone.

A mobile phone may be readily available to a test user. In addition, a modern mobile phone has strong computing power, and is a connected device, which allows for encryption and broadcasting of the test results to targeted receivers.

According to another aspect, there is provided an assay kit comprising:

a test device as provided above; and a computer program product as provided above and/or a computing device as provided above.

The test strip may comprise:

a sample path for promoting even and controlled distribution of the sample, controlling the rate at which liquid enters device, preventing flooding of the device and/or modulating flow properties;

a conjugate path impregnated with conjugate molecules; and/or an absorbent path, the absorbent path acts as a waste tank or reservoir to receive fluid which has flowed laterally along the test strip and to prevent back-flow of sample liquid.

The test strip may be a replaceable part of the test device. If the test strip is replaceable, the detectors and/or other components of the device may be reusable. Reusable components could be advantageous e.g. where a large number of tests are performed in the same location e.g. a hospital.

The test strip may be integral with the test device. If the test strip is integral with the device, the device may be simpler and therefore easier to operate.

The test device may further comprise a display adapted to display the calculated amount of analyte and/or outputs from the optical detectors.

This can enable the test result to be communicated to user in a clear way on the device.

According to another aspect, there is provided a system comprising:

a test device as provided above; and a second device for receiving and processing the (processed) detector outputs.

The second device may receive the (processed) outputs by wire or wirelessly.

The second device could receive the raw data or processed data by wire or wirelessly and act as a display/data processing host, where the test results can be displayed, archived and/or forwarded to relevant people/professionals. For example, the second device could encrypt and broadcast the test results to targeted receivers.

As will be familiar to the skilled person, the testing process may include a labelling stage, in which the analyte is bound to a reagent having a label thereon. The process may use any of a number of different kinds of labels such as inorganic particles, including metals such as gold, silver, carbon and the like, oxides such as tantalum oxide, iron oxide, silicon oxide and the like and organic particles such as polystyrene and the like. The optical absorbance will generally be dependent on electronic energy levels of the label. The labelling stage may occur in the test device, by means of a conjugate pad, in which the conjugate may comprise the label, or may occur prior to introduction of the analyte into the lateral flow test device.

BRIEF DESCRIPTION OF THE DRAWINGS

Embodiments are described in more detail and by way of non-limiting examples with reference to the accompanying drawings, wherein:

FIG. 2 shows a schematic sectional view of an embodiment of a lateral flow immunoassay test device comprising a lateral flow immunoassay test strip;

FIG. 3 shows a schematic sectional view of an embodiment of a lateral flow immunoassay test device without a test strip;

DETAILED DESCRIPTION

Figure 1:
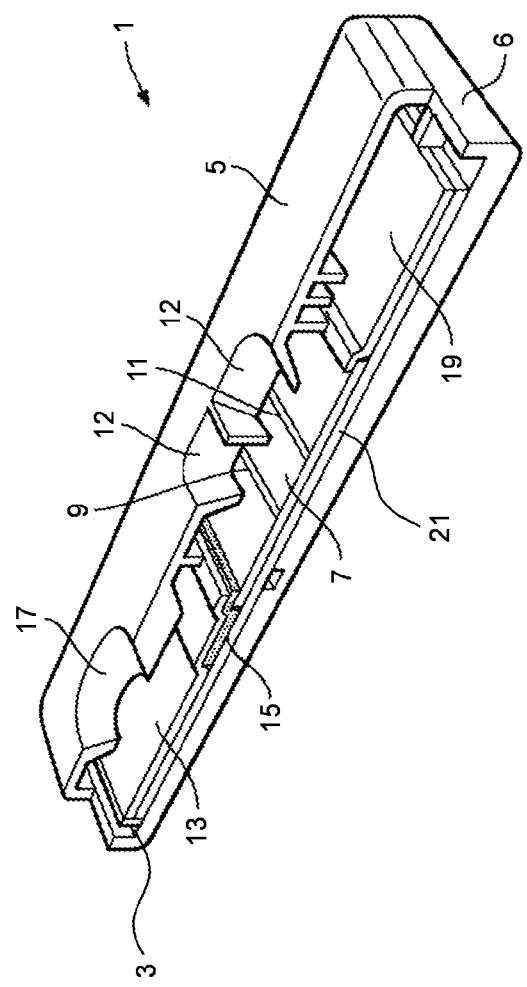
FIG. 1 shows a schematic cutaway perspective view of a prior art lateral flow immunoassay test device.

It should be understood that the Figures are merely schematic and are not drawn to scale. It should also be understood that the same reference numerals are used throughout the Figures to indicate the same or similar parts.

As the present specification relates to the modification of prior art lateral flow immunoassays, it is apposite to first discuss them. FIG. 1 shows such a conventional lateral flow immunoassay test device, indicated generally at 1.

These devices are commercially available and depending on the chemistry can be used for monitoring ovulation, detecting infectious disease organisms, analyzing drugs of abuse, measuring other analytes important to human physiology, and the like. A number of products have also been introduced for veterinary testing, agricultural applications, environmental testing, and food and feed product quality evaluation.

The nature of the chemical reactions that take place on the test strip 3 is not especially relevant to the present disclosure and is not described in further detail for the sake of brevity only. Such chemistry is discussed in, for example, WO 2013/083686.

The prior art device 1 comprises a lateral flow immunoassay test strip 3, mounted in a housing 5. The housing comprises a top housing 5, shown longitudinally cut away, and a bottom housing 6.

Although not required, many lateral flow strips are placed into plastic housings. The housing can prevent the user from applying the sample anywhere except the sample path. In over-the-counter products for urine analysis, the housing also serves to protect the strip from inadvertent splash onto the membrane. Housings can be obtained as off-the-shelf cassettes or custom-designed to fit around the strip.

The test strip 3 comprises a membrane 7 having a test zone 9 and a control zone 11.

The membrane 7 binds capture reagents at the test and control zones 9,11. The test and control zones 9,11 may form part of a sandwich assay or a competitive assay. The polymer from which the membrane 7 is made determines most of its binding characteristics. The membrane 7 may be made of any suitable materials, such as nitrocellulose, polyvinylidene fluoride, (charge-modified) nylon or polyethersulfone, for example. Nitrocellulose is particularly common.

The test zone 9 and the control zone 11 are viewed through windows 12 which allow the user to visualize the presence or absence of the lines 9,11 with the naked eye.

The test strip 3 also comprises a sample path 13 and a conjugate path 15. The sample path 13 is for promoting even and controlled distribution of the sample, controlling the rate at which liquid enters device, preventing flooding of the device and modulating flow properties. The conjugate path 15 is impregnated with conjugate molecules.

The housing 5 comprises a sample port 17 for applying a test liquid to the sample path 13.

The test strip 3 also comprises an absorbent path 19. The absorbent path 19 acts as a waste tank or reservoir to receive fluid which has flowed laterally along the test strip and to prevent back-flow of sample liquid.

The membrane 7, the sample path 13, the conjugate path 15 and the absorbent path 19 are mounted on a backing foil 21. The foil 21 can provide mechanical strength and can enable easier handling of the membrane during manufacture.

In the case of a lateral flow test device targeted for testing whether a specific molecule is present in urine, the physical form of the device is generally such as to be conveniently held by the user whilst passing urine. The requirement that the device may be conveniently handheld imposes minimum requirements on the thickness and width of the device: conversely, there may be competing requirements to minimise the bill of materials, which provides a downward pressure on the thickness and width of the device, and to provide sufficient volume in both the conjugate pad 15 and the test and control zones 9,12 to provide adequate sensitivity provides a lower limit on the dimensions.

The prior art device shown in FIG. 1 is designed for visual inspection: that is to say the user inspects both the test zone and control zone at the end of the testing, which appear as lines on the membrane 7 if labelled reagent has accumulated there.

However, it is known that a visual inspection is a subjective matter, and it has been found that, in some circumstances, the results from as many as one in four tests are incorrectly read by the user.

FIG. 2 shows a possible embodiment of a lateral flow immunoassay device, indicated generally at 101.

The lateral flow immunoassay test device 101 comprises a lateral flow immunoassay test strip 103.

The test strip 103 comprises a test membrane 107 having a translucent section 108 including a control zone 111 and a test zone 109. The translucent section 108 may have a first major surface 131 and a second major surface 133 opposite the first major surface 131. The device 101 is adapted to house the test strip 103 such that the first major surface 131 is exposed to ambient light.

The test device 101 comprises a backing structure 134 for backing the test strip 103. The backing structure 134 comprises a first optical detector 135 for detecting ambient light which has passed through the test zone 109 and a second optical detector 137 for detecting ambient light which has passed through the translucent section 108 in a further zone 110 outside of the test and control zones 109,111. The respective sensing surfaces of the first detector 135 and the second detector 137 may face the second major surface 133.

The device 101 is adapted to house the test strip 103 such that the first optical detector 135 is aligned with the test zone 109 and the second optical detector 139 is aligned with the further zone 110. The test strip 103 is also housed such that the first and second optical detectors 135, 137 detect ambient light after it has passed through the translucent section 108. The test strip 103 may also be housed such that the detectors 135, 137 detect ambient after it has passed through the second major surface 133.

Detection of the combination of the ambient light which has passed through the test zone 109 and the ambient light which has passed through the further zone 110 may be advantageous. In particular, detection of the combination can provide additional information over and above that provided by mere detection of light which has passed through the test zone. For example, it may be possible to calculate a flow rate of the test liquid through the test membrane 107, knowing the flow rate it may be possible to calculate a volume of sample analysed, it may be possible to calculate absorbance due solely to the accumulation of the relevant labelled reagents present in the test zone 109 (e.g. it may be possible to compensate for the effect of a coloured sample or inter-batch variations in membrane opacity), knowledge of the absorbance due solely to the accumulation of the relevant labelled reagents may enable calculation of the amount of labelled reagent present in the test zone, knowledge of the amount of labelled reagent present in the test zone and the volume of sample analysed may enable the calculation of the concentration of an analyte in the test sample.

As the membrane 107 of the test 101 is filled with test liquid, the translucency of the membrane typically changes, e.g. it becomes more translucent. This can be detected by a sudden change in the amount of light passing through the test membrane 107. By knowing the distance between the test zone 109 where the first detector 135 is and the further zone 110 where the second detector 137 is, the flow rate of test liquid can be calculated, e.g., by dividing (i) the volume of sample in the region between the test zone 109 and the further zone 110 by (ii) the time between the changes in translucency at the test zone 109 and the further zone 110.

Further, assuming that the flow rate varies in a typical way over time (e.g. exponential decay), using the calculated flow rate and by measuring the amount of time which has elapsed it may be possible to determine the amount of sample which has passed through the test zone, e.g. by fitting the calculated flow rate and measured elapsed time to predicted (assumed) variations in flow rate.

As labelled reagents are accumulated at the test zone 109 of the membrane 107, the amount of ambient light to pass through the test zone 109 will be reduced. By comparing the output of the first optical detector and the second optical detector, it may be possible to determine the absorbance at the test zone 109 due solely (or at least mainly) to the accumulation of the labelled reagents, e.g., the effect of a coloured sample or inter-batch variations in membrane opacity can be compensated for. This can enable an amount of labelled reagent accumulated at the test zone to be determined more accurately.

The determination of the amount of labelled reagent in the test zone 109 can enable calculation of an amount of analyte present in the sample, for example, for a given amount of sample, in most sandwich assays the amount of labelled reagent in the test zone 109 will be proportional to the amount of analyte in the sample and in some competition assays the amount of labelled reagent in the test zone 109 will be inversely proportional to the amount of analyte in the sample.

Further, information regarding the amount of analyte present in the sample together with the determined volume may permit quantification of the test result as a concentration by dividing the amount of analyte in the sample by the volume of sample which has passed through the test zone.

The development of signal over time also carries information about the kinetics of the reaction. In some circumstances this information can also be used for diagnostic purposes.

Further, this device can enable multiplexing for the detection of multiple analytes in one test. For example, there may be two or more test zones, e.g. the presence of a first analyte in the sample may lead to the accumulation of a first labelled reagent in a first test zone and the presence of a second analyte in the sample may lead to the accumulation of a second labelled reagent in a second test zone. The absorbance in both test zones may be detected using two detectors, one for each test zone, and the second detector discussed above. As a further example, if the presence of a first analyte R leads to red absorbance from a first labelled reagent in the test zone and a second analyte B leads to blue absorbance a second labelled reagent in the test zone. Then, by detecting the ambient light which has passed through the test zone and observing whether red or blue light is present relative to the ambient light which has passed through the further zone, it is possible to determine whether one or both of the analytes R and B are present in the test sample and, further in combination with for instance flow rate information, to obtain a quantitative result as previously explained.

As explained above, in the context of the present specification, detecting light includes the detection of a light intensity distribution over space, time and wavelength. Further, detecting light also includes the detection of the intensity of all light incident on a detector to which the detector responds. The detection of light also includes the detection of an integral of (the intensities of) all visible wavelengths (e.g. 390 nm to 700 nm), the detection of an integral of (the intensities of) a broad visible wavelength band (e.g. violet light, 380 to 450 nm; blue light, 450 to 495 nm; green light, 495 to 570 nm; yellow light, 570 to 590 nm; orange light, 590 to 620 nm; and/or red light, 620 to 750 nm) and the detection of (the intensities of) broad wavelength bands (e.g. a 200 nm, 150 nm, 100 nm, or 50 nm band) or small wavelength bands (e.g. a 25 nm, 20 nm, 10 nm or 5 nm band). For the detection of multiple analytes multiple wavelength bands may be detected. It is not essential that the ambient light which is detected consist of or comprise visible light.

Since the precise required measurement conditions may not be known a priori, it may not be possible to determine an optimum measurement wavelength in order to determine the absorbance of one or each of the first, second and/or third detectors. In particular, the absorbance of the labelled reagent(s) may not be precisely known. A higher signal-to-noise ratio (SNR) may be obtainable at one wavelength compared to that obtainable at a different wavelength. It may therefore be beneficial to measure the absorbance at more than one wavelength.

In example embodiments of the measurement wavelengths are swept across a range of wavelengths, in order to determine an optimum wavelength, at which the sensitivity is highest.

The first, second and/or third detectors, may be swept through the range of wavelengths independently, or at the same time. All of the measurements may be made using a range of wavelengths, or the wavelength may be swept during an initial measurement phase, and thereafter only the optimum wavelength used.

The detecting of ambient light which has passed through the test zone 109, the further zone 110 and/or, if detected, the control zone 111 may comprise detecting ambient light over a period of time and transmitting the time-dependent outputs to the processor.

As detailed herein, the timing of the (relative) changes detected by the first, second and/or third detectors may be advantageous, accordingly, in embodiments the device may be configured to measuring the time-dependant difference between the first, second and/or third detector outputs.

In the device 101 of FIG. 2 the whole of the membrane 107 is translucent, i.e. the section between the conjugate path 115 and the absorbent path 119 is the translucent section 108. However, it is sufficient that only a section or portion 108 of the membrane 107 containing the test and control zones 109, 111 is translucent. The translucent portion 108 need not be continuous, e.g. there may be a non-translucent portion between the test zone 109 and the control zone 111.

That the portion 108 is translucent means that light can pass through the portion 108; therefore, a transparent portion is within the definition of a translucent portion.

The test strip 103 may comprise a sample path 113 for promoting even and controlled distribution of the sample, controlling the rate at which liquid enters device, preventing flooding of the device and modulating flow properties, as is known per se.

The test strip 103 may also comprise a conjugate path 115 impregnated with conjugate molecules, as is known per se.

An absorbent path 119 may also be provided to act as a waste tank or reservoir to receive fluid which has flowed laterally along the test strip and to prevent back-flow of sample liquid, as is known per se.

In at least some embodiments, the backing structure 134 of the test device 101 also comprises a third optical detector 139 for detecting ambient light which has passed through the control zone 111. The device 101 is also adapted to house the test strip 103 such that the third optical detector 139 is arranged to detect ambient light after it has passed through the translucent section 108. The test strip 103 may also be housed such that the third detector 139 detects ambient light after it has passed through the second major surface 133.

As labeled reagents are accumulated at the control zone 111 of the membrane 107, the amount of ambient light to pass through the control zone 111 will be reduced, this can indicate whether the test has completed successfully, in an analogous manner to the determination of the amount of analyte present in the sample discussed above.

As discussed above, changes in translucency of the test zone 109 and the further zone 110 can be detected and the flow rate of test liquid may be determined. Alternatively, the volume of sample in the region between the further zone 110 and the control zone 111 and the time between the changes in translucency at the further zone 110 and the control zone 111 could be used. Another alternative would be to use both volumes (between the test zone 109 and further zone 110 and between the further zone 110 and the control zone 111) and time intervals together (between the test zone 109 and further zone 110 and between the further zone 110 and the control zone 111) and, for example, fit the data to an appropriate, e.g. exponential decay, curve. This can provide more data points to determine the amount of sample which has passed through the test zone.

The test strip 103 may comprise a transparent membrane backing foil 121. This can enable easier handling of the membrane 107 during manufacture. The backing foil 121 may also act as a barrier to contamination e.g. from adhesives used to mount the membrane 107. The backing foil 121 is typically 50 µm to 150 µm thick, e.g. around 100 µm thick.

The external surface 123 of the membrane backing foil 121 may have a matt texture. This increases light diffusion when the membrane is dry and increases the difference between dry and wet in terms of transparency to light, thereby providing a greater contrast between wet and dry.

Regardless of whether the membrane backing foil 121 is present, the test strip 103 may be held in place against the membrane backing structure 134 with a glue or adhesive layer.

The first, second and/or third optical detectors 135, 137, 139 may be integrated into the membrane backing structure 134 of the test device 101, such that the detector is in close proximity with the test strip surface. Selection of the correct spacing between the detector and the test strip surface requires careful consideration, in particular, it is necessary to avoid fouling of the sensor (which can occur if the sensor is too close to the test strip), however, light pollution for undesired zones may be more likely leak into the detector if it is too far away from the strip. For example, when the test strip is housed in the test device the detector may be less than 5 mm, 3 mm, 2.5 mm, 2 mm, 1.5 mm, 1 mm, 1.0 mm, 0.75 mm, 0.50 mm, or 0.25 mm away from the test strip.

This is a simple construction which does not require a complex optical path. Further, the transition moment from dry to wet of the membrane may be reliably detected with this arrangement. Further, in this way only ambient light which has passed through the correct zone 109, 110, 111 may reach the respective detector 135, 137, 139, such that the effects of light pollution may be mitigated.

The membrane backing structure 134 maybe of plastics or of any other suitable alternative material.

In at least some embodiments, the backing structure 134 may comprise a first sensor comprising a first array of detectors, wherein the first optical detector 135 is one of the detectors of the first array.

This means that it is not necessary for the test zone 109 to be in exact registration with a detector of the array. Rather, the test zone 109 may be in registration with a detector 135. This is relevant as it can be difficult to place a test zone 109 at a particular, pre-defined, location of a test membrane 107. Therefore, use of such a sensor allows greater tolerance in the placement of the test zone 109 on the membrane 107.

The detectors of the array may be individually readable, such that the outputs may be individually processable.

The backing structure 134 may comprise a second sensor comprising a second array of detectors, wherein the second optical detector 137 is one of the detectors of the second array.

As above, this can provide greater tolerance in the positioning of the various zones 109, 110, 111 on the test membrane 107.

The detectors of the second array may be individually readable, such that the outputs may be individually processable.

If the third detector is present, the backing structure 134 may comprise a third sensor comprising a third array of detectors, wherein the third optical detector 139 is one of the detectors of the third array.

As above, this can provide greater tolerance in the positioning of the control zone 111 on the test membrane 107.

The detectors of the third array may be individually readable, such that the outputs may be individually processable.

The first, second and/or third optical detectors 135, 137, 139 may be behind windows to separate the liquids of the lateral flow test strip 103 from the optical detectors 135, 137, 139. This can allow the detectors 135, 137, 139 to be in close proximity with the test strip 103. In this way only ambient light which has passed through the correct zone 109, 110, 111 may reach the respective detector 135, 137, 139.

The test device 101 may comprise a processor 140 adapted to receive the outputs from the optical detectors 135, 137, 139.

The processor 140 may be on the same substrate as the detectors 135, 137, 139; may be in close proximity to the detectors 135, 137, 139; or may be packaged in the same package as the detectors 135, 137, 139. Any other arrangement is also possible.

The processor 140 may be adapted to receive the detected outputs and forward the detected outputs to an antenna, i.e. to function essentially as an amplifier/transmitter.

The processor 140 may be adapted to receive the detected outputs and to then carry out basic processing operations, e.g. filtering, before then forwarding the detected outputs to an antenna.

The processor 140 may be adapted to receive the detected outputs and then to compare the second output from the first and/or third output and then to forward these new calculated outputs to an antenna.

The processor 140 may be further adapted to further process the detected or new calculated outputs and to calculate an amount of analyte in a test liquid, as described above. This can enable calculation of a test result on the device 101 itself.

The raw data and/or calculated results may then be forwarded to another processor or device and/or displayed on a display, e.g. a display forming part of the test device 101 (the test device 101 may thus be self-contained and directly read by a user) or of another device receiving the raw data and/or calculated results from the test device 101.

Combinations of the above may also be applicable, for instance without limitation, a read-out on the device 101 may be combined with communication to an external device and thence to a computer of a medical professional for further analysis and/or follow-up with the patient. The lateral flow test device 101 may further comprise a battery or other energy storage means. Such a battery may allow the test device 101 to store data or test results for, for instance, later display, analysis, or transmission, whether wirelessly or wired. In the case of wireless and wired transmission, power for the transmission—and even in embodiments for data processing—may be provided by the receiving device. The arrangement may include other functionality. For example and without limitation, the processor may include means to date-stamp or time-stamp to indicate the moment of a test, and shelf-life indication to provide confirmation as to whether the test was carried out within an approved time-window. A unique or other identifier may be added to the test data, in order to personalise it or encrypt it or provide further security for the data.

The processor 140 may be integrated in close proximity to the lateral flow test strip 103.

The test device 101 may comprise an antenna 143 for wirelessly transmitting the (processed) outputs, wherein the processor 140 is adapted to supply the antenna 143 with the (processed) outputs.

The test device 101 may comprise an antenna 143 and may be combined with a second device for wirelessly receiving and processing the (processed) outputs to form a system.

The test device 101 may comprise a port and may be combined with a second device for receiving by wire and processing the (processed) outputs to form a system.

The second device could receive the raw data or processed data by wire or wirelessly and act as a display/data processing host, where the outputs may be (further) processed, the test results may be displayed, archived and/or forwarded to relevant people/professionals. For example, the second device could encrypt and broadcast the test results to targeted receivers.

The test device 101 may comprise a display 145 adapted to display the calculated amount of analyte. This can enable the test result to be communicated to user in a clear way on the device.

The test device 101 may further comprise a housing (not shown) including a window for allowing ambient light to enter the housing and pass through the translucent section 108. This provides a housing to protect the test strip and/or backing structure of the test device. The window may be a transparent substrate, e.g. plastic or glass, or it may be an opening in the housing.

This can eliminate the need for an additional, often expensive, additional light source. The use of a window, in contrast to a dedicated, active, light source such as a LED, is possible because subtracting the second detector output from the first obtains a relative measurement. In this way the device adjusts to differing ambient lighting conditions. Whilst the disclosed device does not require a dedicated light source, such a light source may never-the-less be present, for example to provide a device which functions in a dark environment or to increase the accuracy of the measurement.

Similarly a relative measurement can be obtained by comparing the second detector output with that of the third detector output in respect of the control zone 111.

The device disclosed herein enables the detection of the flow rate. This can be combined with other methods for liquid flow detection to increase accuracy or to lower the cost of the test, e.g., with the capacitive lateral flow test arrangement and method disclosed in PCT/EP2012/074624 published as WO 2013/083686.

FIG. 3 shows an embodiment of a test device 101 without the test strip 103. The test strip 103 is a replaceable part of the test device 101. As the test strip 103 is replaceable, the detectors 135, 137, 139 and/or other components 134, 140, 143, 145 of the device may be reusable. Reusable components could be advantageous e.g. where a large number of tests are performed in the same location e.g. a hospital.

Alternatively, the test strip 103 may be integral with the test device 101. If the test strip 103 is integral with the device 101, the device 101 is simpler and therefore easier to operate.

In embodiments, functionality to measure or check environmental conditions such as temperature or humidity, which may have an impact on the test results, may be included.

Figure 4:
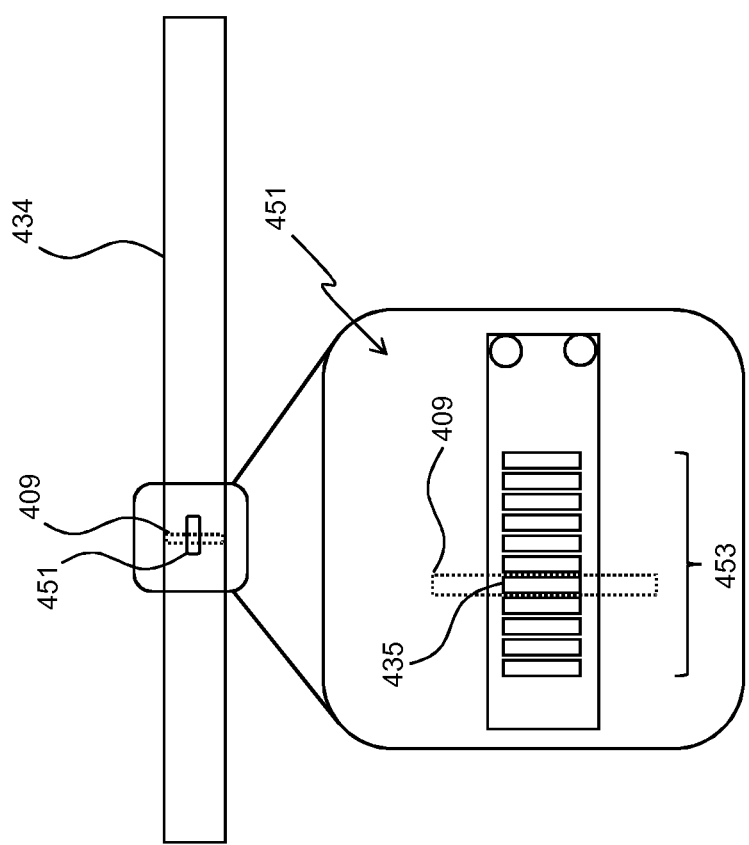
FIG. 4 shows a schematic plan view of an embodiment of a membrane backing structure comprising an example optical sensor comprising an array of optical detectors.

FIG. 4 shows an example sensor 451 comprising a detector array 453. The sensor 451 is part of a membrane backing structure 434. The membrane backing structure 434 may consist of or comprise flex-foil.

The location 409 of a test zone of a test strip is indicated in FIG. 4. Typically, the test zone may be 1 mm wide. However, a test zone is generally only placed on the test membrane with a positioning accuracy of around 2 mm. Further, depending on the chemistry of the lateral flow immunoassay test strip, the test zone may not be visible before the test is used. Therefore, in order to ensure that a detector can detect light which has passed through the test zone, as shown in the example of FIG. 4, the backing structure 434 may comprise a first sensor 451 comprising a first array of detectors 453, wherein the first optical detector 435 is one of the detectors of the first array 453.

The sensor 451 may comprise an array 453 of eleven detectors. Each detector of the array may have a sensing surface of 500 µm×200 µm and the detector may be 1 mm×3.5 mm. The detectors of the array 453 may be placed adjacent each other. This can provide a positioning tolerance for the location 409 of the test zone of 2 mm.

As will be apparent, this means that it is not necessary for the location 409 of the test zone to be in exact registration with a detector. Rather, the location 409 of the test zone may be in registration with any one of the detectors 435. Therefore, use of such a sensor allows greater tolerance in the placement of the test zone on the membrane, thereby overcoming the problem that it can be difficult to ensure that the location 409 of the test zone is in alignment with the first detector.

The detectors of the array 453 which make up the sensor 451 may be individually readable, such that the outputs may be individually processable.

The detector array 451 is described with reference to a first optical detector 435 and the location 409 of a test zone on the test strip. However, a similar sensor and detector array may be used to provide the second optical detector and/or third optical detector in registration with a further zone and/or test zone, respectively. As will be apparent, this will bring similar advantages to using the array to provide the first detector.

The optical sensors may be integrated into the membrane backing structure 434 of the test device, as described above.

Further, the optical sensors may be behind windows to separate the liquids of the lateral flow test strip from the optical detectors, as described above.

With reference to FIG. 2, an embodiment of a lateral flow immunoassay test device 101 is operated as follows. A test liquid is applied to the sample path 113 of the test strip 103. The first major surface 131 of the translucent section 108 is illuminated with ambient light. Ambient light which has passed through the test zone 109 is detected using the first optical detector 135. Ambient light which has passed through the translucent section in a further zone 110 outside of the test and control zones is detected using the second optical detector 137. The detector outputs are then transmitted to a processor.

The amount of analyte in the test liquid can then be calculated using the detector outputs, as discussed above.

Further, ambient light passing through the control zone 111 and emitted from the second major surface 133 can be detected.

The processor to which the outputs are transmitted may be part of the device 101 or the processor may be the processor of a second device, e.g. a mobile phone.

If the processor is part of the device 101 it may be adapted merely to receive the outputs and forward the outputs to an antenna or to carry out a greater degree of processing, as described above.

Figure 5:
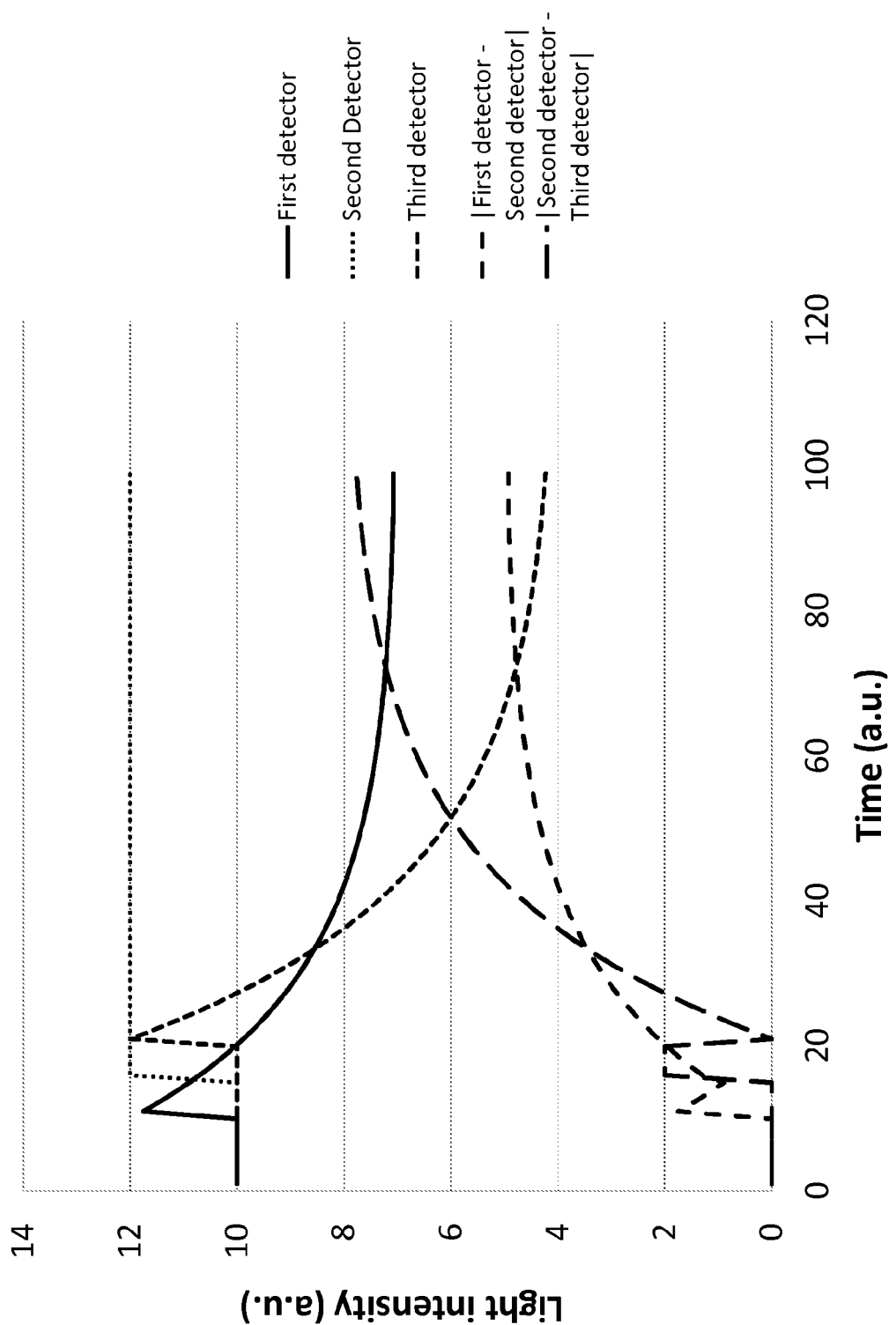
FIG. 5 shows a plot of signal evolution over time of the three detectors of the test device of FIG. 2 in use.

FIG. 5 demonstrates graphically how the detector outputs vary with time, where t=0 corresponds to the beginning of the test. FIG. 5 maps the intensity of light at all wavelengths emitted from the second major surface 133.

However, depending upon the assay used light may be detected at only a single wavelength. If it is desired to use a multiplexed assay for detection of multiple analytes in one test several figures like that of FIG. 5 could be plotted, each for light passing through differing areas of a test membrane or of different wavelengths. As discussed above and below, the detector outputs may be compared relative to each other in order to determine information about the test strip and hence the test liquid. Therefore if light is measured only at a single wavelength or a narrow range of wavelengths, to allow easy comparison of the detector outputs it may be preferred for the first, second and third detectors to detect the same or similar wavelength(s).

The light intensity at the first optical detector 135 can be seen to be constant, until such time as the solvent front reaches the test zone 109 detector 135 when there is a sudden increase in transmission (decrease in absorbance). Then as the test continues and labelled reagent accumulates at the test zone 135 the light intensity decreases (increasing absorbance).

The light intensity at the second optical detector 137 can be seen to be constant, until such time as the solvent front reaches the zone 110 above the detector 137 when there is a sudden increase in transmission (decrease in absorbance). Then as the test continues the light intensity remains at this new higher level.

The light intensity at the third optical detector 139 can also be seen to be constant until the solvent front reaches the control zone 111 when there is a sudden increase in transmission (decrease in absorbance). As the test continues, labelled reagent accumulates at the control zone 111 and the light intensity decreases (absorbance increases).

The test signal is also shown in FIG. 5. The test signal is the modulus of the detected light intensity of the first optical detector 135 less the light intensity at the second optical detector 137. After initial anomalies relating to the arrival of the solvent front at the first and second detectors 135, 137 at different times, the test signal can be seen to increase asymptotically. This signal increases asymptotically because the amount of labelled reagent in the test zone 109 increases asymptotically. I.e. the test signal at any one time is proportional to the amount of labelled reagent present in the test zone 109 at that time.

The control signal is also shown in FIG. 5. The control signal is the modulus of the detected light intensity of the third optical detector 139 less the light intensity at the second optical detector 137. After initial anomalies relating to the arrival of the solvent front at the first and second detectors 135, 137 at different times, the control signal can be seen to increase asymptotically. In a similar way to the test signal, this signal increases asymptotically because the amount of labelled reagent in the control zone 111 increases asymptotically. That is, the control signal at any one time is proportional to the amount of labelled reagent present in the control zone 111 at that time. As might be expected and shown in FIG. 5, the control signal is of a greater magnitude than the test signal, indicating that a greater amount of labelled reagent is present in the control zone 111 than the test zone 109 (assuming that the test and control labelled reagents have the same absorbance).

The method disclosed herein enables detection of the flow rate. This can be combined with other methods for liquid flow detection to increase accuracy or over all lower cost of the complete test. For example, the method disclosed herein may be combined with the capacitive method disclosed in WO 2013/083686.

A number of detectors were tested to demonstrate that transition measurements are suitable for the devices and methods discussed above. Nitrocellulose membranes were impregnated with varying amounts of 100 nm colloidal gold solutions. First major surfaces of the nitrocellulose membranes were illuminated with light and detectors were used to measure the light output from second major surfaces.

The detector outputs for six different detectors for differing amounts of solution are shown in Table 1. The detector outputs were recorded whilst the membranes were still wet. As can be seen from Table 1, an increase in concentration of colloidal gold results in a decrease in the detector output for each detector.

TABLE 1

| Conc. a.u. | d1 | d2 | d3 | d4 | d5 | d6 |
|---|---|---|---|---|---|---|
| 0 | 1003 | 1025 | 1047 | 1067 | 1552 | 2035 |
| 5 | 1007 | 1019 | 1043 | 1067 | 1540 | 2028 |
| 10 | 956 | 972 | 992 | 1012 | 1457 | 1921 |
| 15 | 890 | 910 | 922 | 948 | 1355 | 1788 |
| 25 | 841 | 861 | 875 | 897 | 1283 | 1683 |

Table 2 shows outputs for the same detectors after the solutions have been allowed to dry. As can be seen from Table 2, an increase in concentration of colloidal gold results in a decrease in the detector output for each detector.

TABLE 2

| Conc. a.u. | d1 | d2 | d3 | d4 | d5 | d6 |
|---|---|---|---|---|---|---|
| 0 | 331 | 347 | 355 | 347 | 522 | 637 |
| 5 | 300 | 316 | 324 | 331 | 469 | 568 |
| 10 | 268 | 284 | 291 | 297 | 520 | 504 |
| 15 | 253 | 268 | 276 | 281 | 394 | 471 |
| 25 | 247 | 264 | 270 | 277 | 285 | 461 |

There is also provided a method of processing on a processor detector outputs of the method of operating a test device (described above). The method comprises processing the outputs on a processor to determine an amount of analyte in a test liquid.

In an analogous way to the device and method of operating a lateral flow immunoassay described above, processing the combination of the first detector output (light which has passed through the test zone 109) and the second detector output (light which has passed through the further zone 110) together may be advantageous.

The method may comprise calculating a flow rate of test liquid through the test membrane.

As detailed above, as the membrane 107 of the test 101 is filled with test liquid, the translucency of the membrane typically changes, e.g. it becomes more translucent and this can enable the flow rate of test liquid to be calculated.

The method may comprise calculating a volume of sample analysed.

As detailed above, assuming that the flow rate varies in a typical way over time (e.g. exponential decay), using the calculated flow rate and by measuring the amount of time which has elapsed it may be possible to determine the amount of sample which has passed through the test zone.

The method may comprise subtracting the second detector output from the first and/or third detector output.

As labelled reagents are accumulated at the test zone 109 of the membrane 107, the amount of ambient light to pass through the test zone 109 will be reduced. By subtracting the second detector output from the first detector output, it may be possible to determine the absorption at the test zone 109 due solely (or at least mainly) to the accumulation of the labelled reagent of interest, e.g., the effect of a coloured sample or inter-batch variations in membrane opacity can be compensated for. This can enable an amount of labelled reagent accumulated at the test zone to be determined more accurately.

Accordingly, the method may comprise calculating the amount of labeled reagent present in the test zone.

The determination of the amount of labelled reagent in the test zone 109 can enable calculation of the amount of analyte present in the sample, as detailed above.

The method may comprise calculation of the concentration of an analyte in the test sample.

Information regarding the amount of analyte present in the sample together with the determined volume may permit quantification of the test result as a concentration by dividing the amount of analyte in the sample by the volume of sample which has passed through the test zone.

The method may comprise calculating the amount of labelled reagent accumulated at the control zone.

This can indicate whether the test has completed successfully.

The method may comprise forwarding the calculated results to another processor or device and/or displaying the results on a display.

This can enable the results to be communicated to a user or other device for further processing.

There is also provided a computer program product comprising computer-readable storage means comprising computer program code for, when executed on one or more processors of a computing device, implementing a method of processing described above.

The storage means may be any suitable storage means such as a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a magnetic storage device, or any suitable combination of the foregoing.

There is provided a computing device including at least one processor and a computer program product described above wherein at least one processor is adapted to execute the code of said product.

The computing device may be any one of a large number of different computing devices. Consumer electronics devices having significant computing power for executing the computer program product have increased in popularity, such that it is common for an individual to own a number of such devices. A particularly prevalent computing device suitable for executing the computer program product is a mobile phone.

The computing device may be a mobile phone. A mobile phone is usually available to a test user. In addition, a modern mobile phone has a very strong computing power, and is a connected device, which allows for encryption and broadcasting of the test results to targeted receivers.

The computing device may be a desktop computer, a laptop computer, a personal organiser, a music player, a tablet, a phablet or a dedicated processing device. These devices are prevalent and readily available in a number of environments.

There is also provided an assay kit comprising a device as described above and a computer program product and/or a computing device as described above.

For example, the assay kit could comprise:

a device as described above and a computer program product as described above on a suitable storage means;

a device as described above and a computing device including a computer program product as described above, wherein the computing device is a dedicated spectral processing device;

a device as described above and a computing device including the computer program product as described above, wherein the computing device is a mobile phone.

It should be noted that the above-mentioned embodiments illustrate rather than limit the claims, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The embodiments can be implemented by means of hardware comprising several distinct elements. A single processor or other unit may fulfil the functions of several items recited in the claims. A computer program may be stored/distributed on a suitable medium, such as an optical storage medium or a solid-state medium supplied together with or as part of other hardware, but may also be distributed in other forms, such as via the Internet or other wired or wireless telecommunication systems. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A lateral flow immunoassay test device comprising:
   a lateral flow immunoassay test strip having a test membrane;
      wherein the test membrane includes a translucent section, the translucent section having a first surface and a second surface;
      wherein the translucent section includes a control zone, a further zone and a test zone;
      wherein the first surface of the translucent section is configured to receive ambient light; and
   a backing structure coupled to the second surface of the translucent section, and including a first optical detector and a second optical detector;
      wherein the first optical detector is coupled to receive the ambient light through the second surface and test zone, and
      wherein the second optical detector is coupled to receive the ambient light through the second surface and the further zone.

2. The test device according to claim 1, wherein the backing structure further comprises a third optical detector coupled to receive the ambient light through the second surface and the control zone.

3. The test device according to claim 1, further comprising a housing including a window configured to pass the ambient light to the translucent section of the test membrane.

4. The test device according to claim 1, wherein the test strip includes a transparent membrane backing foil coupled to the test membrane; and wherein an external surface of the transparent membrane backing foil has a matte texture.

5. The test device according to claim 1, wherein the backing structure further includes:
   a first sensor including a first array of detectors, wherein the first optical detector is one of the detectors of the first array; and
   a second sensor including a second array of detectors, wherein the second optical detector is one of the detectors of the second array.

6. The test device according to claim 1,
   further comprising a processor configured to receive output signals from the optical detectors, and
   wherein the processor is configured to process said output signals.

7. The test device according to claim 6,
   further comprising an antenna for wirelessly transmitting the processed output signals, and
   wherein the processor is configured to supply the antenna with said processed outputs.

8. A method of operating a lateral flow immunoassay test device, comprising: providing a test device according to claim 1, the test device further including a test strip; applying a test liquid to the test strip; illuminating the translucent section with ambient light; detecting ambient light which has passed through the test zone with the first optical detector; detecting ambient light which has passed through the translucent section in the further zone with the second optical detector; and transmitting outputs of the detectors to a processor.

9. The method according to claim 8, wherein the backing structure further comprises a third optical detector for detecting ambient light which has passed through the control zone, and the method further comprises detecting ambient light which has passed through the control zone with the third optical detector.

10. The method according to claim 8, wherein the detecting of ambient light which has passed through the test zone, the further zone and/or, if detected, the control zone comprises detecting ambient light over a period of time and transmitting the time-dependent outputs to the processor.

11. The method according to claim 8, wherein the test device comprises the processor; and wherein the method further comprises processing outputs of the detectors on the processor to determine an amount of analyte in the test liquid.

12. A method of determining an amount of analyte in a sample, the method comprising: receiving detector outputs transmitted by a method in accordance with claim 8; and processing the outputs on a processor to determine an amount of analyte in the test liquid.

13. A computer program product comprising computer-readable storage means comprising computer program code for, when executed on one or more processors of a computing device, implementing a method of determining an amount of analyte in a sample, the method comprising: receiving detector outputs transmitted in accordance with a method of operating a lateral flow immunoassay test device, including providing a test device according to claim 1, the test device further including a test strip; applying a test liquid to the test strip; illuminating the translucent section with ambient light; detecting ambient light which has passed through the test zone with the first optical detector; detecting ambient light which has passed through the translucent section in the further zone with the second optical detector and transmitting outputs of the detectors to a processor; and processing the outputs on a processor to determine an amount of analyte in the test liquid.

14. A computing device including at least one processor and the computer program product of claim 13 wherein at least one processor is adapted to execute the code of said product, optionally wherein the computing device is a mobile phone.

15. An assay kit comprising: a test device; and a computer program product of claim 13.

* * * * *